(12) United States Patent
Rogers et al.

(10) Patent No.: US 8,131,367 B2
(45) Date of Patent: *Mar. 6, 2012

(54) SYSTEM AND METHOD FOR MONITORING POWER SOURCE LONGEVITY OF AN IMPLANTABLE MEDICAL DEVICE

(75) Inventors: Charles R. Rogers, Maple Grove, MN (US); Donald R. Merritt, Brooklyn Center, MN (US); Craig L. Schmidt, Eagan, MN (US); Mukul Jain, Woodbury, MN (US)

(73) Assignee: Medtronic, Inc., Minneapolis, MN (US)

( * ) Notice: Subject to any disclaimer, the term of this patent is extended or adjusted under 35 U.S.C. 154(b) by 299 days.

This patent is subject to a terminal disclaimer.

(21) Appl. No.: 12/432,974

(22) Filed: Apr. 30, 2009

(65) Prior Publication Data

US 2009/0210034 A1   Aug. 20, 2009

Related U.S. Application Data

(63) Continuation of application No. 11/138,062, filed on May 25, 2005, now Pat. No. 7,542,801, which is a continuation of application No. 10/409,039, filed on Apr. 7, 2003, now Pat. No. 6,901,293.

(51) Int. Cl.
*A61N 1/00* (2006.01)
(52) U.S. Cl. ........................................................ 607/29
(58) Field of Classification Search ...................... 607/29
See application file for complete search history.

(56) References Cited

U.S. PATENT DOCUMENTS

| | | | |
|---|---|---|---|
| 4,026,305 A | 5/1977 | Brownlee et al. | 128/419 |
| 4,041,955 A | 8/1977 | Kelly et al. | 128/419 |
| 4,071,032 A | 1/1978 | Schulman | 128/419 |
| 4,082,097 A | 4/1978 | Mann et al. | 128/419 |
| 4,124,533 A | 11/1978 | Knowles et al. | 252/431 |
| 4,248,237 A | 2/1981 | Kenny | 128/419 |
| 4,254,775 A | 3/1981 | Langer | 128/419 |
| 4,313,079 A | 1/1982 | Lee | 320/48 |

(Continued)

FOREIGN PATENT DOCUMENTS

EP    0 593 198    4/1994

(Continued)

OTHER PUBLICATIONS

Medtronic, Inc., *SynchroMed® Infusion System*, product brochure (1995).

*Primary Examiner* — George Manuel
(74) *Attorney, Agent, or Firm* — IPLM Group, P.A.

(57) ABSTRACT

Power source longevity monitor for an implantable medical device. An energy counter counts the amount of energy used by the implantable medical device. An energy converter converts the energy used into an estimate of remaining power source longevity and generating an energy longevity estimate. A voltage monitor monitors the voltage of the power source. A voltage converter converts the voltage monitored by the voltage monitor into an estimate of remaining longevity of the power source and generating a voltage longevity estimate. A calculator is operatively coupled to the energy converter and to the voltage converter and predicts the power source longevity using the energy longevity estimate early in the useful life of the power source and using the voltage longevity estimate later in the useful life of the power source.

18 Claims, 6 Drawing Sheets

U.S. PATENT DOCUMENTS

| | | | | |
|---|---|---|---|---|
| 4,373,527 A | 2/1983 | Fischell | ........................ | 128/260 |
| 4,390,020 A | 6/1983 | Herpers | ........................ | 128/419 |
| 4,448,197 A | 5/1984 | Nappholz et al. | ............. | 128/419 |
| 4,542,532 A | 9/1985 | McQuilkin | ..................... | 455/78 |
| 4,550,370 A | 10/1985 | Baker | .......................... | 364/413 |
| 4,556,061 A | 12/1985 | Barreras et al. | ............... | 128/419 |
| 4,677,363 A | 6/1987 | Kopmann | ....................... | 320/44 |
| 4,692,147 A | 9/1987 | Duggan | .................... | 604/891.1 |
| 5,080,096 A | 1/1992 | Hooper et al. | ................ | 128/419 |
| 5,107,833 A | 4/1992 | Barsness | ...................... | 128/419 |
| 5,117,825 A | 6/1992 | Grevious | ...................... | 128/419 |
| 5,127,404 A | 7/1992 | Wyborny et al. | ............. | 128/419 |
| 5,168,871 A | 12/1992 | Grevious | ...................... | 128/419 |
| 5,292,343 A | 3/1994 | Blanchette et al. | ............. | 607/32 |
| 5,314,450 A | 5/1994 | Thompson | ..................... | 607/32 |
| 5,324,315 A | 6/1994 | Grevious | ....................... | 607/60 |
| 5,344,431 A | 9/1994 | Merritt et al. | .................. | 607/29 |
| 5,350,411 A | 9/1994 | Ryan et al. | ...................... | 607/32 |
| 5,354,319 A | 10/1994 | Wyborny et al. | ............. | 607/32 |
| 5,369,364 A | 11/1994 | Renirie et al. | ................. | 324/430 |
| 5,370,668 A | 12/1994 | Shelton et al. | .................. | 607/29 |
| 5,383,909 A | 1/1995 | Keimel | ............................ | 607/7 |
| 5,391,193 A | 2/1995 | Thompson | ..................... | 607/29 |
| 5,402,070 A | 3/1995 | Shelton et al. | ................. | 324/433 |
| 5,402,794 A | 4/1995 | Wahlstrand et al. | .......... | 128/696 |
| 5,458,624 A | 10/1995 | Renirie et al. | .................. | 607/29 |
| 5,591,217 A | 1/1997 | Barreras | ........................ | 607/61 |
| 5,620,474 A | 4/1997 | Koopman | ....................... | 607/29 |
| 5,693,076 A | 12/1997 | Kaemmerer | ................... | 607/59 |
| 5,741,307 A | 4/1998 | Kroll | .............................. | 607/5 |
| 5,741,313 A | 4/1998 | Davis et al. | ...................... | 607/36 |
| 5,744,931 A | 4/1998 | Arai et al. | ........................ | 320/43 |
| 5,752,976 A | 5/1998 | Duffin et al. | .................... | 607/32 |
| 5,764,034 A | 6/1998 | Bowman et al. | .............. | 320/155 |
| 5,766,232 A | 6/1998 | Grevious et al. | ................. | 607/60 |
| 5,769,873 A | 6/1998 | Zadeh | ............................. | 607/29 |
| 5,769,877 A | 6/1998 | Barreras, Sr. | ................... | 607/61 |
| 5,807,397 A | 9/1998 | Barreras | ......................... | 607/61 |
| 5,861,019 A | 1/1999 | Sun et al. | ......................... | 607/60 |
| 5,904,708 A | 5/1999 | Goedeke | ........................ | 607/18 |
| 5,925,068 A | 7/1999 | Kroll | ............................... | 607/29 |
| 5,994,876 A | 11/1999 | Canny et al. | ................... | 320/132 |
| 6,016,448 A | 1/2000 | Busacker et al. | ............... | 607/29 |
| 6,099,495 A | 8/2000 | Kinghorn et al. | ............... | 604/93 |
| 6,108,579 A | 8/2000 | Snell et al. | ....................... | 607/29 |
| 6,148,235 A | 11/2000 | Kuiper | ............................ | 607/29 |
| 6,154,675 A | 11/2000 | Juran et al. | ...................... | 607/29 |
| 6,166,518 A | 12/2000 | Echarri et al. | ................. | 320/106 |
| 6,167,309 A | 12/2000 | Lyden | ............................. | 607/29 |
| 6,185,461 B1 | 2/2001 | Er | .................................. | 607/27 |
| 6,198,968 B1 | 3/2001 | Prutchi et al. | ..................... | 607/9 |
| 6,272,379 B1 | 8/2001 | Fischell et al. | ..................... | 607/5 |
| 6,400,988 B1 | 6/2002 | Gurewitsch | ..................... | 607/29 |
| 6,490,484 B2 | 12/2002 | Dooley et al. | ..................... | 607/5 |
| 6,584,355 B2 | 6/2003 | Stessman | ........................ | 607/29 |
| 6,648,823 B2 * | 11/2003 | Thompson | .................... | 600/300 |
| 6,671,552 B2 | 12/2003 | Merritt et al. | .................... | 607/29 |
| 2002/0161328 A1 | 10/2002 | Rogers | ............................ | 604/67 |
| 2003/0065366 A1 | 4/2003 | Merritt et al. | .................... | 607/27 |

FOREIGN PATENT DOCUMENTS

| | | |
|---|---|---|
| WO | WO 91/10471 | 7/1991 |
| WO | WO 96/20754 | 11/1996 |
| WO | WO 00/24459 | 5/2000 |
| WO | WO 01/05466 | 1/2001 |
| WO | WO 01/08749 | 8/2001 |
| WO | WO 02/074368 | 9/2002 |

* cited by examiner

SYSTEM AND METHOD FOR MONITORING POWER SOURCE LONGEVITY OF AN IMPLANTABLE MEDICAL DEVICE

This application is a continuation application of U.S. patent application Ser. No. 11/138,062, filed May 25, 2005, which is a continuation application of U.S. patent application Ser. No. 10/409,039, filed Apr. 7, 2003, now U.S. Pat. No. 6,901,293, and claims priority therefrom.

FIELD OF THE INVENTION

The present invention relates generally to power source monitors and, more particularly, to power source monitors for implantable medical devices having a power source having a voltage which declines over its useful life.

BACKGROUND OF THE INVENTION

The medical device industry produces a wide variety of electronic and mechanical devices for treating patient medical conditions. Depending upon the medical condition, medical devices can be surgically implanted or connected externally to the patient receiving treatment. Clinicians use medical devices alone or in combination with therapeutic substance therapies and surgery to treat patient medical conditions. For some medical conditions, medical devices provide the best, and sometimes the only, therapy to restore an individual to a more healthful condition and a fuller life.

One type of medical device is an implantable therapeutic substance infusion device. An implantable therapeutic substance infusion device is implanted by a clinician into a patient at a location appropriate for the therapy. Typically, a therapeutic substance infusion catheter is connected to the device outlet and implanted to infuse the therapeutic substance such as a drug or infusate at a programmed infusion rate and predetermined location to treat a condition such as pain, spasticity, cancer, and other medical conditions. Many therapeutic substance infusion devices are configured, so the device can be replenished with therapeutic substance through a septum while the device is implanted, so the time the device can be implanted may not be limited by therapeutic substance capacity. An example of an implantable therapeutic substance infusion is shown in Medtronic, Inc. product brochure entitled "SynchroMed™ Infusion System" (1995).

Other implantable devices exist which electrically stimulate neurological tissue to treat or relieve the symptoms of a wide variety of physiological or psychological maladies or pain. Such devices are typically part of systems that are entirely implantable within the patient or are partially implantable and partially external to the patient. Systems that are entirely implantable in the patient typically include an implantable pulse generator and an extension and lead or leads. In such a system, the implantable pulse generator, extension and lead are entirely implanted in the bodies of the patients. An example of such a system is the Itrel™ 3 system manufactured and sold by Medtronic, Inc. of Minneapolis, Minn. Because the implantable pulse generator is implanted, the power sources needed to power the implantable pulse generator are also implanted. Typically, the power source for an implantable pulse generator is a battery.

Each of these implantable devices delivers a therapeutic output to the patient. In the case of an implantable therapeutic substance infusion device, the therapeutic output can be a therapeutic substance which is infused into the patient. In the case of a neurological tissue stimulator, the therapeutic output is an electrical signal intended to produce a therapeutic result in the patient. Other types of implantable therapeutic delivery devices also exist including cardiac pacemakers and defibrillators.

Electrically powered implanted therapeutic delivery devices can require replacement once implanted due to factors such as battery consumption, corrosive damage and mechanical wear. Since replacement of the implanted therapeutic delivery device requires an invasive procedure of explanting the existing device and implanting a new device, it is desirable to only replace the therapeutic delivery device when replacement is required. Replacement of previously implanted therapeutic delivery devices was typically scheduled based upon a worst-case statically forecasted elective replacement period. The worst-case scenario typically resulted in the implanted therapeutic delivery device being replaced several months or even years before the implanted therapeutic delivery device actually required replacement.

Some previous implantable pulse generators such as pacemakers have monitored a single sensed battery condition to estimate replacement time for the implanted device or battery such as shown in U.S. Pat. No. 6,167,309, Lyden, entitled "Method For Monitoring End Of Life For Battery" (Dec. 26, 2000).

Battery monitors which monitor the voltage of the battery in order to determine, or to predict, the remaining longevity of the battery have an inherent shortcoming. The voltage of a battery will commonly very slowly decline over time with only a slight variation in the voltage until the voltage the battery nears the end of its useful life. As the battery nears the end of its useful life, the battery voltage will begin to decline at a greater rate, often dramatically. Such a battery is advantageous as a source of power for an implantable therapeutic delivery device because the battery delivers such an assured relatively constant voltage over most of the useful life of the device. However, such a battery creates a problem for a battery longevity monitor using the voltage of the battery in an attempt to determine the longevity of the battery. Since the battery voltage remains relatively constant over most of the life of the battery, it is difficult to predict whether the battery is in the early part of the relatively flat voltage curve or nearing the end of the relatively flat voltage curve. The difference, of course, is a marked difference in the predicted longevity of the battery.

The ability to accurately predict the remaining longevity of the power source of an implantable therapeutic delivery device enables the patient to receive maximum life from the device and minimize the frequency, and possibly the number, of explantation and reimplantation of the device simply for the replacement of the power source. Further, since some safety margin is usually built in and because the patient usually schedules any such explantation and reimplantation, often around a busy schedule, additional time off of the actual remaining longevity of the power source may be lost.

For the foregoing reasons, there is a need for an implantable therapeutic delivery device with active longevity prediction to increase the implantable therapeutic delivery device's effective life, reduce the need for a clinician to perform static longevity forecasts for therapy changes, facilitate elective replacement scheduling for the convenience of the patient and clinician, and many other improvements.

BRIEF SUMMARY OF THE INVENTION

While voltage monitors for determining the longevity of a power source in an implantable therapeutic delivery device are not accurate (due to the flat voltage curve) in the early portion of the life of the power source, such a voltage monitor can be very accurate near the end of the useful file of the power source (because of the steepening of the voltage curve).

Another technique for estimating the longevity of a power in an implantable therapeutic delivery device is to measure, or estimate, the amount of energy actually consumed by the implantable therapeutic delivery device. Since the initial fresh charge of the power source can be known, and hence its useful life or longevity can be known, if the amount of energy used by the implantable therapeutic delivery device can be measured or estimated, then the remaining longevity, or useful life, of the implantable therapeutic delivery device can be estimated simply by subtracting the amount of energy used from the initial known amount of energy contained in the power source.

The amount of energy used can be estimated by any number of techniques such as counting the number of operations performed by the implantable therapeutic delivery device, the amount of therapeutic substance infused, the energy in the electrical stimulation pulses delivered, the number of rotations of a drug infusion pump, the length of time the device is operated and the current flowing from the power source, among others. It is recognized, however, that the estimate of the amount of energy used by the implantable therapeutic delivery device is only an estimate and is not usually an exact measure. Typically, the measurement or estimate of the amount of energy is only a certain percentage accurate, or, in other words, the measurement or estimate has a percentage amount of error. The trouble is that the amount of error in actually measuring the amount of energy which has been consumed is cumulative over time as the implanted therapeutic delivery device is operated.

Thus, while measuring or estimating the amount of energy used by the implantable therapeutic delivery device can be very accurate in the early stages of the useful life of the power source, the accuracy declines over time as the quantitative amount of cumulative error builds up over time.

While the technique of counting the amount of energy used by the implantable therapeutic delivery device is accurate during the early portion of the useful life of the power source, this technique is increasingly inaccurate during the later stages of the useful life of the power source. While the technique of monitoring the voltage of the power source can be very accurate during the later stages of the useful life of the power source as the voltage curves more steeply declines, this technique is inherently inaccurate during the earlier portion of the useful life of the power source while the voltage curve is relatively flat.

These two techniques can be combined, however, to produce a power source longevity monitor having improved accuracy across the entire useful life of the power source. Using the technique of energy counting earlier in the useful life of the power source significantly improves accuracy over the technique of monitoring voltage and using the technique of monitoring voltage later in the useful life of the power source significantly improves accuracy over the technique of energy counting.

The result is a system and method for monitoring the longevity of the power source of an implantable therapeutic delivery device which is more accurate than prior art systems and methods achieving increased usefulness of the implantable therapeutic delivery device before explanation and reimplantation is required.

In one embodiment, the present invention provides an implantable medical device for delivering a therapeutic output to a patient. An electrical power source has a useful life and a voltage which declines over the useful life. A therapeutic delivery device is operatively coupled to the power source and adapted to deliver the therapeutic output to the patient. A power source longevity monitor is operatively coupled to the power source and the therapeutic delivery device. An energy counter counts the amount of energy used by the implantable medical device. An energy converter converts the energy used into an estimate of remaining power source longevity and generating an energy longevity estimate. A voltage monitor monitors the voltage of the power source. A voltage converter converts the voltage monitored by the voltage monitor into an estimate of remaining longevity of the power source and generating a voltage longevity estimate. A calculator is operatively coupled to the energy converter and to the voltage converter and predicts the power source longevity using the energy longevity estimate early in the useful life of the power source and using the voltage longevity estimate later in the useful life of the power source.

In another embodiment, the present invention provides a method of monitoring longevity of an electrical power source in an implantable medical device capable of delivering a therapeutic output to a patient, having an electrical power source having a useful life and a voltage which declines over the useful life and a therapeutic delivery device operatively coupled to the power source and adapted to deliver the therapeutic output to the patient. The amount of energy used by the implantable medical device is determined. The amount of energy used is converted into an estimate of power source longevity and an energy longevity estimate is generated. The voltage of the power source is monitored. The voltage is converted into an estimate of power source longevity and a voltage longevity estimate is generated. The power source longevity is predicted using the energy longevity estimate early in the useful life of the power source and using the voltage longevity estimate later in the useful life of the power source.

In a preferred embodiment wherein the power source longevity is indicated.

In a preferred embodiment wherein the power source longevity comprises a remaining useful life of the power source.

In a preferred embodiment wherein the power source longevity comprises an amount of useful life of the power source already consumed.

In a preferred embodiment wherein the energy converter converts the energy used into an energy longevity estimate by accumulating a count of an amount of energy used by the implantable medical device over at least a portion of the useful life of the power source.

In a preferred embodiment wherein the energy longevity estimate is obtained from a look-up table using the amount of energy used.

In a preferred embodiment the energy longevity estimate is obtained using a predetermined mathematical algorithm as a function of the amount of energy used.

In a preferred embodiment, the voltage longevity estimate is obtained from a look-up table using the voltage.

In a preferred embodiment, the voltage longevity estimate is obtained using a predetermined mathematical algorithm as a function of the voltage.

In a preferred embodiment, the energy longevity estimate is used until the voltage longevity estimate is more accurate than the energy longevity estimate.

In a preferred embodiment wherein the energy longevity estimate is used until approximately ninety percent of the useful life of the power source is consumed.

DETAILED DESCRIPTION OF THE INVENTION

The entire content of U.S. patent application Ser. No. 11/138,062, filed May 25, 2005, and U.S. patent application Ser. No. 10/409,039, filed Apr. 7, 2003, now U.S. Pat. No. 6,901,293, are hereby incorporated by reference.

Figure 1:
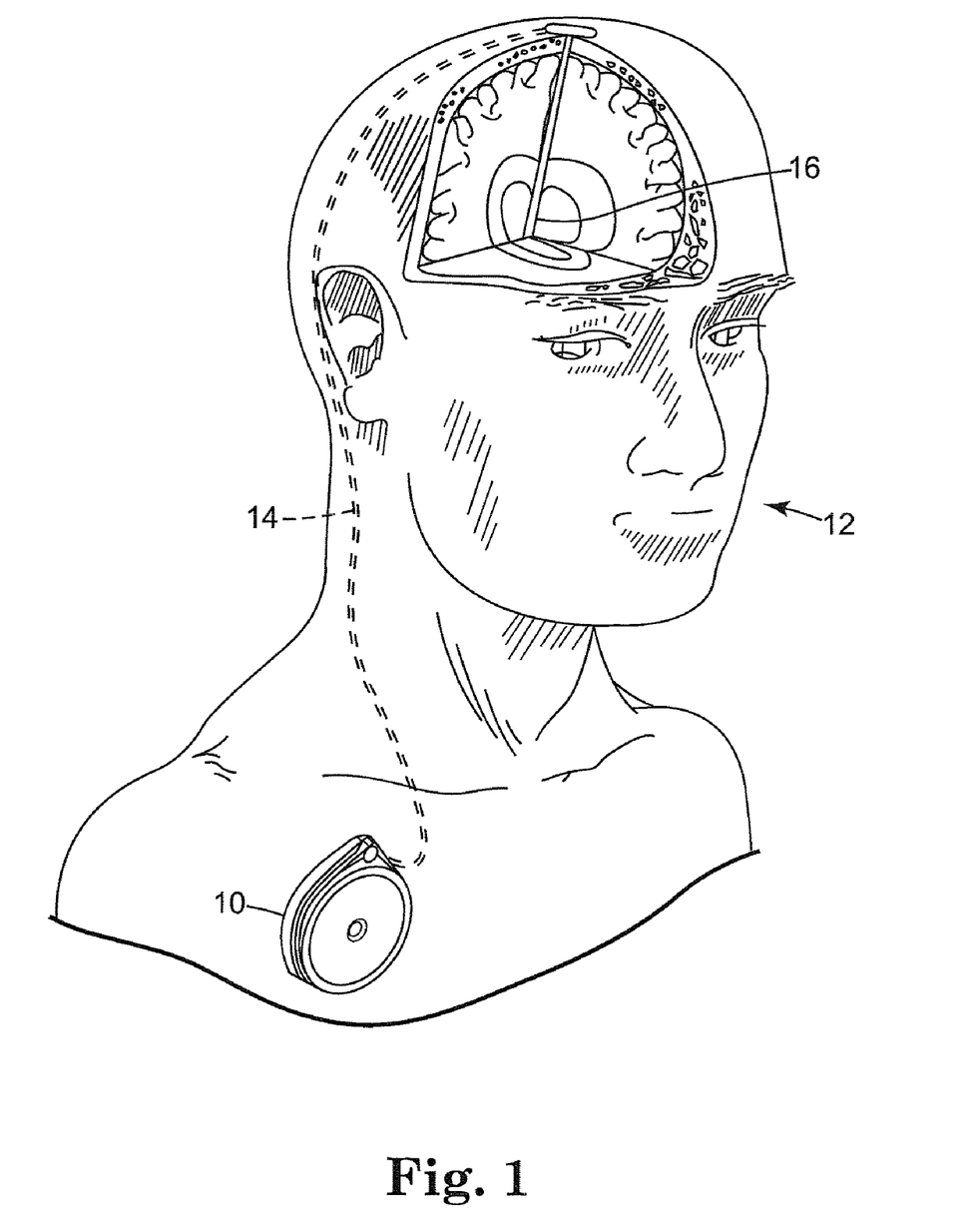
FIG. 1 illustrated an implantable therapeutic delivery device in accordance with the present invention implanted in a patient.

FIG. 1 shows implantable therapeutic delivery device 10, for example, a drug pump, implanted in patient 12. The implantable therapeutic delivery device 10 is typically implanted by a surgeon in a sterile surgical procedure performed under local, regional, or general anesthesia. Before implanting the therapeutic delivery device 10, a catheter 14 is typically implanted with the distal end position at a desired therapeutic delivery site 16 and the proximal end tunneled under the skin to the location where the therapeutic delivery device 10 is to be implanted. Implantable therapeutic delivery device 10 is generally implanted subcutaneous about 2.5 centimeter (1.0 inch) beneath the skin where there is sufficient tissue to support the implanted system. Once therapeutic delivery device 10 is implanted into the patient 12, the incision can be sutured closed and therapeutic delivery device 10 can begin operation.

Therapeutic substance delivery device 10 operates to infuse a therapeutic substance into patient 12. Therapeutic substance delivery device 10 can be used for a wide variety of therapies such as pain, spasticity, cancer, and many other medical conditions.

The therapeutic substance contained in therapeutic substance delivery device 10 is a substance intended to have a therapeutic effect such as pharmaceutical compositions, genetic materials, biologics, and other substances. Pharmaceutical compositions are chemical formulations intended to have a therapeutic effect such as intrathecal antispasmodics, pain medications, chemotherapeutic agents, and the like. Pharmaceutical compositions are often configured to function in an implanted environment with characteristics such as stability at body temperature to retain therapeutic qualities, concentration to reduce the frequency of replenishment, and the like. Genetic materials are substances intended to have a direct or indirect genetic therapeutic effect such as genetic vectors, genetic regulator elements, genetic structural elements, DNA, and the like. Biologics are substances that are living matter or derived from living matter intended to have a therapeutic effect such as stem cells, platelets, hormones, biologically produced chemicals, and the like. Other substances may or may not be intended to have a therapeutic effect and are not easily classified such as saline solution, fluoroscopy agents, disease diagnostic agents and the like. Unless otherwise noted in the following paragraphs, a drug is synonymous with any therapeutic, diagnostic, or other substance that is delivered by the implantable infusion device.

Implantable therapeutic delivery device 10 can be any of a number of therapeutic delivery devices such as an implantable therapeutic substance delivery device, implantable drug pump, cardiac pacemaker, cardioverter or defibrillator, as examples.

Figure 2:
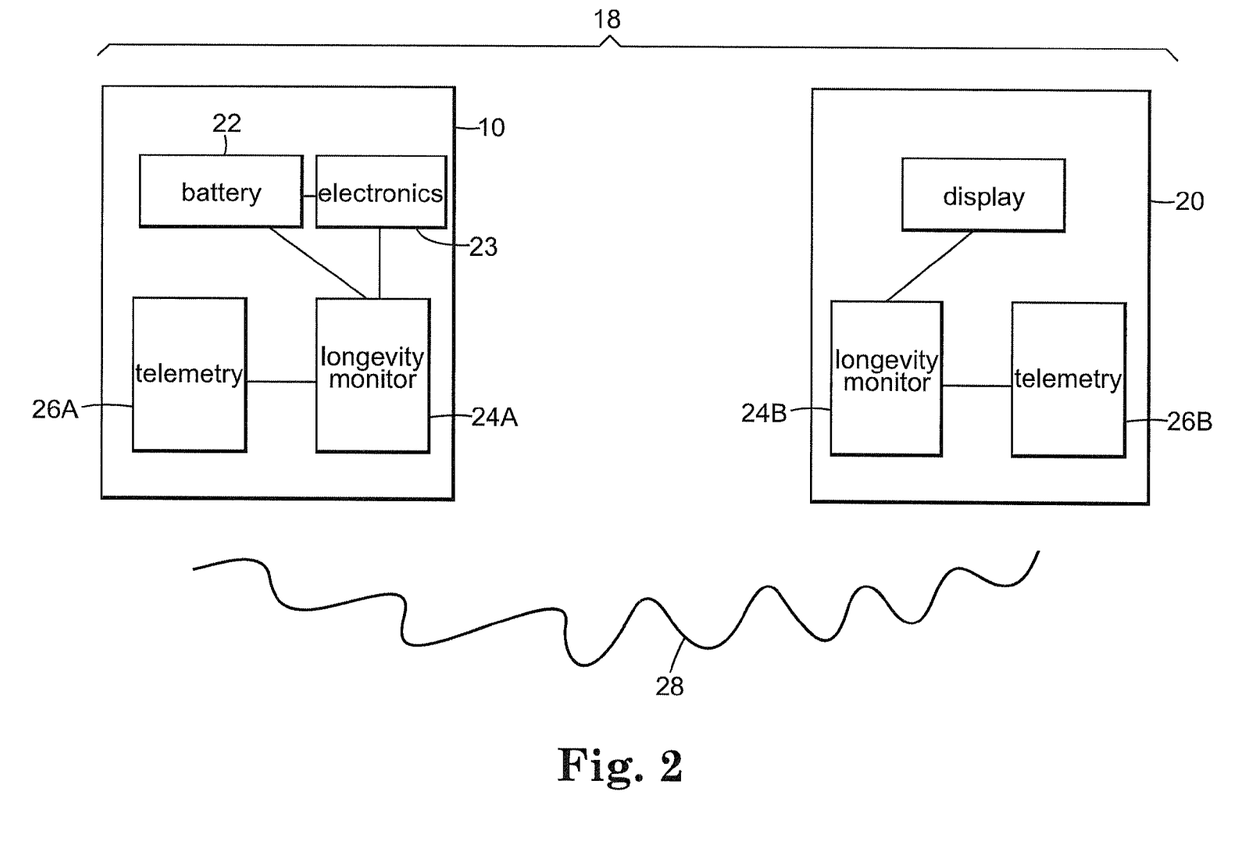
FIG. 2 is a block diagram illustrating the functional distribution of an embodiment of a system the present invention between an implantable therapeutic delivery device and an external unit.

A system 18 for delivering therapeutic output, e.g., substance or electrical, to patient 12 is illustrated in FIG. 2. System 18, in a preferred embodiment, comprises two main components, implantable therapeutic delivery device 10 and an associated external unit 20. Implantable therapeutic delivery device 10 is powered by a power source, in this case, battery 22. Battery 22 powers electrical componentry 23 of therapeutic delivery device 10 such as a substance delivery pump and associated control electronics including pump control circuitry. Such associated electrical components 23 are well known in the art and are not further discussed here for clarity. In this embodiment, at least a portion of longevity monitor 24A located in implantable therapeutic delivery device 10 monitors the condition of battery 22 both through directly monitoring the voltage of battery 22 but also through monitoring the operation of the implantable therapeutic delivery device 10 from electrical components 23. Implantable therapeutic delivery device 10 also has conventional telemetry circuitry 26A for communicating via electromagnetic waves 28 with conventional and complementary telemetry circuitry 26B in external unit 20. Thus, longevity monitor 24B in external unit 20 can communicate with longevity monitor 24A in implantable therapeutic delivery device 10. Longevity monitor 24B may communicate the results of the longevity monitoring to a user, e.g., patient 12 or a medical professional, via display 30.

By communicating via telemetry circuitry 26A and 26B, the longevity monitoring function in system 18 can be split between longevity monitor 24A located in therapeutic delivery device 10 and longevity monitor 24B located in external unit 20, or longevity monitoring functions can be located mostly in therapeutic delivery device 10 or can be located mostly in external unit 20. At least some function should be retained in therapeutic delivery device 10 to monitor the voltage of battery 22. In an embodiment, some function is retained in external unit 20 to communicate the result, e.g., via display 30.

Figure 3:
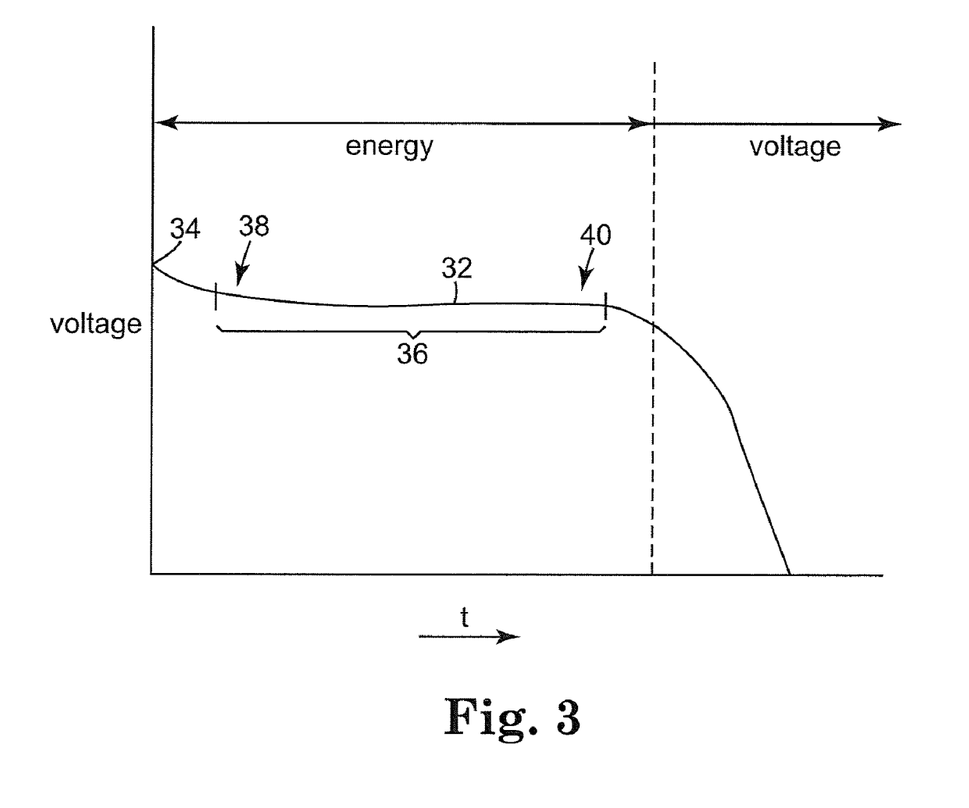
FIG. 3 is a chart illustrating a voltage curve of a power source which can be used in an implantable therapeutic delivery device in accordance with the present invention.

FIG. 3 graphically illustrates an exemplary voltage use curve of a typical battery 22 used to power implantable therapeutic delivery device 10 as the voltage of battery 22 deteriorates over time. Voltage 32 of battery 22 begins its useful life with an initial voltage 34. As battery 22 is initially utilized voltage 32 begins to decline, at first perceptively, until reaching a generally flat portion 36 of voltage curve 32 profile. For most of the useful life of battery 22, voltage 32 remains nearly constant in this flat portion 36 of voltage curve 32. As battery 22 begins to become geriatric, voltage 32 begins to decline more rapidly. Toward the end of the useful of battery 22, voltage 32 falls off dramatically.

Battery chemistries used in a typical battery 22 for implantable therapeutic delivery device 10 are specifically chosen to maintain flat portion 36 of voltage curve 32 for most of the useful life of such battery 22. Such a battery chemistry enables battery 22 to effectively power implantable therapeutic delivery device 10 for a relatively long period of time without significant degradation in the performance of implantable therapeutic delivery device 10 However, near the end of the useful life of battery 22 employing such chemistry, voltage curve 32 drops off dramatically and quickly. The length of time remaining in the useful life of battery 22 once voltage 32 starts to fall dramatically can be, relatively, short.

For conventional battery longevity monitors that rely on measuring the actual voltage 32 of battery 22, this presents a dual problem. First, it is difficult to determine where in flat portion 36 of voltage curve 32, battery 22 currently resides since the voltage measured during the flat portion 36 of voltage curve 32 is generally constant. A battery 22 whose longevity is currently at point 38 on voltage curve 32 would return a voltage that is approximately the same as a battery 22 whose longevity is currently at point 40 on voltage curve 32. This dramatic difference in the remaining longevity of battery 22 is nearly indistinguishable due to flat portion 36 of voltage curve 32. This is especially true when taking into account variations in actual voltages between actual batteries 22. In some battery chemistries, the amount of useful life of battery 22 remaining once its voltage starts to fall dramatically may be only five percent (5%) to ten percent (10%) of the original useful life of battery 22.

Thus, a longevity monitor that relies solely on the measured voltage 32 from battery 22 will, literally, have little idea whether the useful life of battery 22 is at point 38 relatively early in the useful life of battery 22 or at point 40 relatively late in the useful life of battery 22. The difference, of course, can be crucial to patient 12 and to a medical professional monitoring the operation of implantable therapeutic delivery device 10. An implantable therapeutic delivery device 10 with a battery 22 at point 38 on voltage curve 32 will have many hours, days, weeks, months, or even years, of service remaining. Surgery to replace a battery 22 near the end of its useful life need not be scheduled in the relatively near future. However, an implantable therapeutic delivery device 10 with a battery 22 at point 40 will be near the point at which its voltage 32 begins to fall dramatically. Surgery to replace such a battery 22 near the beginning of its useful life should be scheduled relatively quickly. As can be seen, the result can be a significant amount of unnecessary surgeries, or quickly scheduled surgeries, in order to be sure that battery 22 is replaced before its voltage 32 falls dramatically.

Another technique for determining the remaining useful life of battery 22 is to count the amount of energy consumed by implantable therapeutic delivery device 10. Combined with knowledge of the total initial energy content of battery 22, knowing how much energy implantable therapeutic delivery device 10 has consumed since battery 22 was installed, will provide enough information to determine the longevity of battery 22, either the remaining useful life or the proportion of useful life of battery 22 already expended. Such energy counting techniques, such as counting the number of revolutions of a substance pump (for example) or the length of time electrical circuitry has operated (for another example), can be very accurate over relatively short periods of time. The amount of energy consumed each revolution of a substance pump can easily be calculated. Thus, the amount of energy consumed by implantable therapeutic delivery device 10 due to one revolution of the substance pump can be determined with relative accuracy. Similarly, the amount of energy utilized by electrical circuitry 23 for a relatively short period of time, e.g., one day, can also be relatively easily calculated. Adding together all of the individual energy consumptions of implantable therapeutic delivery device 10 over a short period of time yields a fairly accurate determination of the total amount of energy consumed by implantable therapeutic delivery device 10. Since this energy determination does not rely at all on the actual voltage of battery 22, this energy determination is completely independent of and is not frustrated by flat portion 36 of voltage curve 32.

However, estimating the actual amount of energy consumed by implantable therapeutic delivery device 10 is subject to certain errors. For example, each individual substance pump may consume a slightly different amount of energy during a single revolution. Further, the amount of energy consumed during one revolution of a substance pump may vary somewhat over time due to normal wear. While these errors in estimation are small when measured over a single revolution (or few revolutions) of substance pump, whatever error exists tends to accumulate over time. An error in estimating the energy consumed by a revolution of a substance pump could occur for every revolution of the substance pump. Over time, the amount of error builds up and continues to increase. Over a long period of time, for example, over most of the useful life of battery 22, the amount of error in estimating the longevity of battery by estimating the amount of energy consumed by implantable therapeutic delivery device 10 could increase to significant levels. As the remaining useful life of battery 22 declines so will the accuracy of a longevity estimates based upon the amount of energy consumed by implantable therapeutic delivery device 10. Thus, estimating battery 22 longevity by counting the amount of energy consumed by implantable therapeutic delivery device 10 will be most accurate early in the useful life of battery 22 and will decline as time goes along.

The most difficult time to determine longevity of battery 22 using a voltage 32 estimate is during the early portion of the useful life of battery 22. This is because the voltage of battery 22 can be in the flat portion 36 of voltage curve 36. Toward the end of the useful life of battery 22, determining the longevity of battery 22 becomes much more accurate for a voltage based monitoring system.

Figure 4:
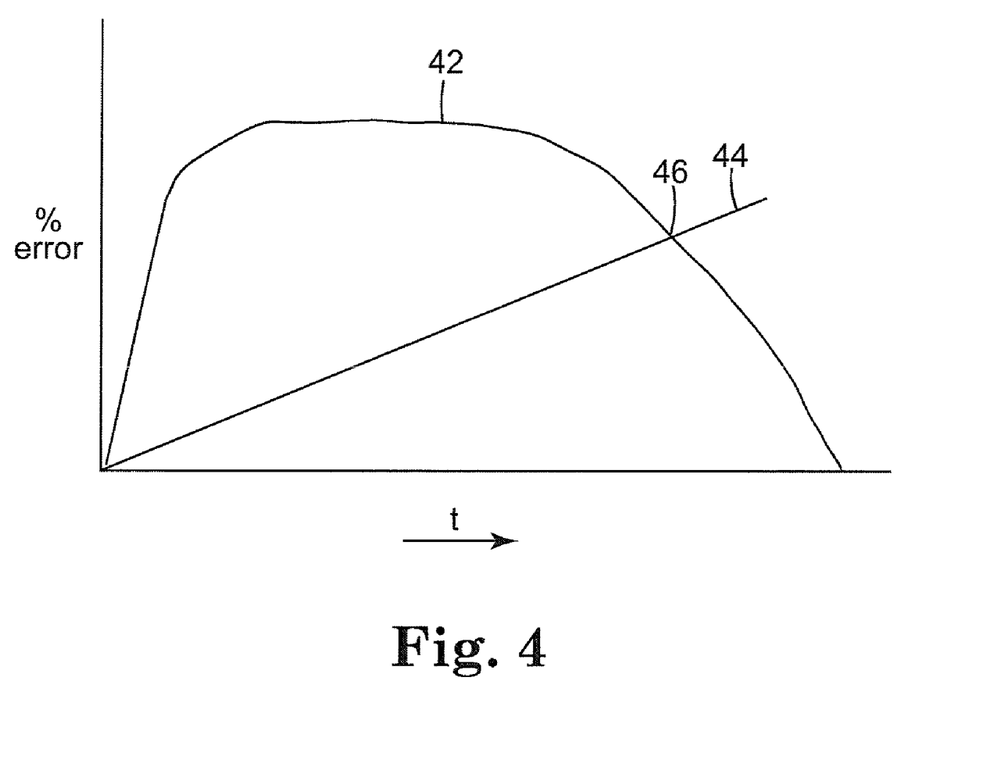
FIG. 4 is a chart illustrating the percentage error between an energy technique of estimation of longevity and a voltage technique of estimation of longevity.

This is illustrated in the chart of FIG. 4 which plots the percentage error over time (useful life) of battery 22 for both a voltage based monitoring system and an energy based monitoring system.

Voltage based error 42 is very low at initial battery use. This is because battery 22 is new and is known to be at the beginning of its useful life. As battery 22 begins to be utilized, its voltage initially drops before entering flat portion 36 (FIG. 3) of voltage curve 32. As voltage curve 32 begins to flatten, however, the percentage error in estimating the longevity increases dramatically due to the flat portion 36 of the voltage curve 36. However, during the later stages of the useful life of battery 22, the percentage error using a voltage based monitoring system falls dramatically. As battery 22 emerges from the flat portion 36 of the voltage curve 32, the voltage of battery 22 can more accurately determine the remaining useful life of battery 22. Of course, when the voltage reaches zero, the longevity of battery 22 is known with certainty.

This is contrasted with energy based error 44 which, as indicated above, begins with a very accurate estimate of the remaining useful life of battery based on very little energy having been consumed by implantable therapeutic delivery device 10. However, as time goes along, the error in estimating the amount of energy actual consumed by implantable therapeutic delivery device 10 continues to accumulate, probably nearly linearly, for the entire useful life of battery 22. It can be seen that while energy based error 44 is much lower than voltage based error 42 during the entire early stages of battery life, that voltage based error is lower than energy based error 44 during the latter stages of battery life. Voltage based error 42 becomes more accurate at cross-over point 46. Following cross-over point 46, in time, voltage based error 42 is lower than energy based error 44. The exact time at which cross-over point 46 occurs is dependent on many variables including the slope of energy based error 44 curve. However, it is known that voltage based error 42 will decline following voltage curve 32 emergence from flat portion 36 of energy curve 32.

Longevity monitor 24A and 24B should use an energy based monitoring system during the early portions of the useful life of battery 22 and should switch to a voltage based monitoring system during the later portions of the useful life of battery 22. It is preferable that longevity monitors 24A and 24B use energy based monitoring techniques before cross-over point 46 and voltage based monitoring techniques following cross-over point 46. Typically, this can be somewhere in the five (5) to ten (10) percent remaining useful battery life point.

Figure 5:
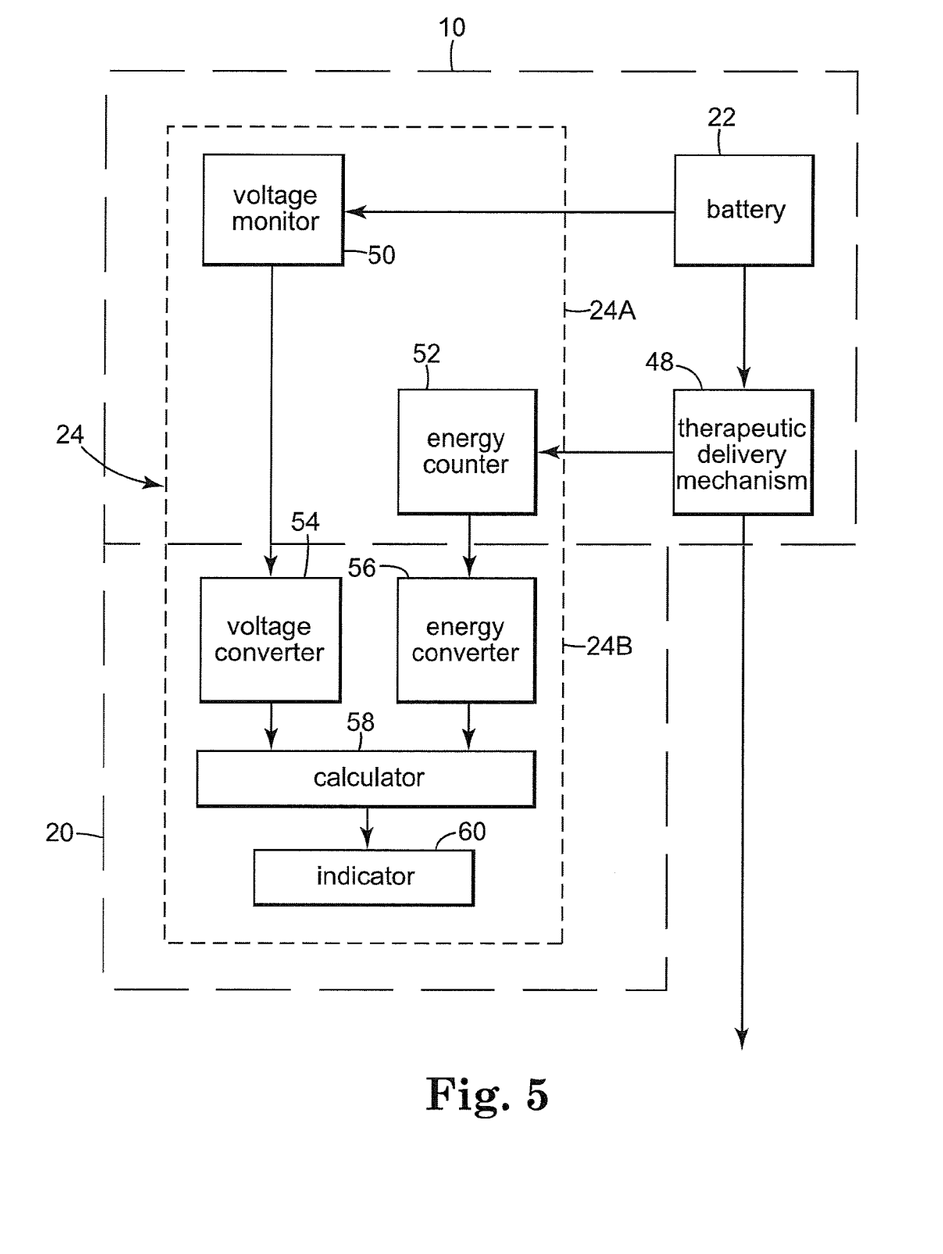
FIG. 5 is a detailed block diagram of a system for estimating longevity of a power source in an implantable therapeutic delivery device.

FIG. 5 is a block diagram of implantable therapeutic delivery device 10 and external unit 20. Implantable therapeutic delivery device 10 contains battery 22 and therapeutic delivery mechanism 48, such as a substance pump or electrical stimulator, which are conventional. Longevity monitor 24 is shown functionally divided into two portions, longevity monitor 24A located in implantable therapeutic delivery device 10 and longevity monitor 24B located in external unit 20. Voltage monitor 50 is operatively coupled to battery 22 in order to monitor the actual output voltage of battery 22. Such voltage monitoring circuits are conventional and are well known. Energy counter 52 monitors characteristics from therapeutic delivery mechanism 48 to estimate the amount of energy consumed by implantable therapeutic delivery device 10. Examples of characteristics which could be monitored include the number of revolutions of a substance delivery pump, the activation of certain electrical circuitry (and, hence, the length of time of activation of such electrical circuitry) and/or the number electrical pulses delivered by an electrical stimulator.

Voltage converter 54 receives information from voltage monitor 50 on the value of the voltage of battery 22. Voltage converter 54 converts the value of the voltage of battery 22 to an estimate of the longevity of battery 22, e.g., the remaining useful life of battery 22. This conversion can be done by any conventional means such as by a look-up table, for example. Alternatively, this conversion can be done by calculation using an algebraic equation.

Similarly, energy converter 56 receives information from energy counter 52 on the amount of energy consumed by implantable therapeutic delivery device 10. Energy converter 56 converts the amount of energy consumed by implantable therapeutic delivery device 10 to an estimate of the longevity of battery 22, e.g., the remaining useful life of battery 22. This conversion can be done by any conventional means such as by a look-up table, for example. Alternatively, this conversion can be done by calculation using an algebraic equation.

The result of both the voltage estimation from voltage converter 54 and the energy estimation from energy converter 56 is passed to calculator 58. Calculator 58 determines the longevity of battery 22 by comparing the result from the voltage estimation from voltage converter 54 and the result from the energy estimation from energy converter 56. As an example, calculator 58 can use either the voltage estimation or the energy estimation depending upon the portion of the useful life of battery 22 remaining. For example, calculator 58 can use the energy estimation during the early portion of the useful life of battery 22 and can use the voltage estimation during the later portion of the useful life of battery 22. Calculator 58 can use the energy estimation until cross-over point 46 is reached and use the voltage estimation thereafter. Alternatively, calculator can use the energy estimation for a fixed percentage of the useful life of battery, e.g., for the first ninety (90) or ninety-five (95) percent of the useful life of battery 22.

Optionally, longevity monitor 24B can communicate the longevity calculated with a conventional indicator 60 such as display 30. Alternatively, longevity monitor 24B may sound an alarm or take other appropriate action once the remaining useful life of battery 22 reaches a predetermined point.

While the elements of longevity monitor 24, including longevity monitor 24A and longevity monitor 24B, have been illustrated as hardware elements, it is to be recognized and understood that all or portions of voltage monitor 50, energy counter 52, voltage converter 54, energy converter 56 and calculator 58 could be implemented as firmware, software or the like. In fact, many combinations are possible.

It is to be recognized and understood that while longevity monitor 24 has been illustrated as being distributed between implantable therapeutic delivery device 10 and external unit 20 in a particular way, that other distributions are possible. For example, if much of the functions of longevity monitor 24 are implemented in software, as is preferred, then these software functions can be implemented in external device 20 where more real estate and greater processing power as well as more energy is available. Alternatively, of course, all of the functions of longevity monitor 24 could be implemented in implantable therapeutic delivery device 10, given available real estate, energy power and processing power. Only the indicator 60 to communicate with the external world would be external and, even then, indicator 60 could be an auditory alarm which also could be internal to implantable therapeutic delivery device 10.

Figure 6:
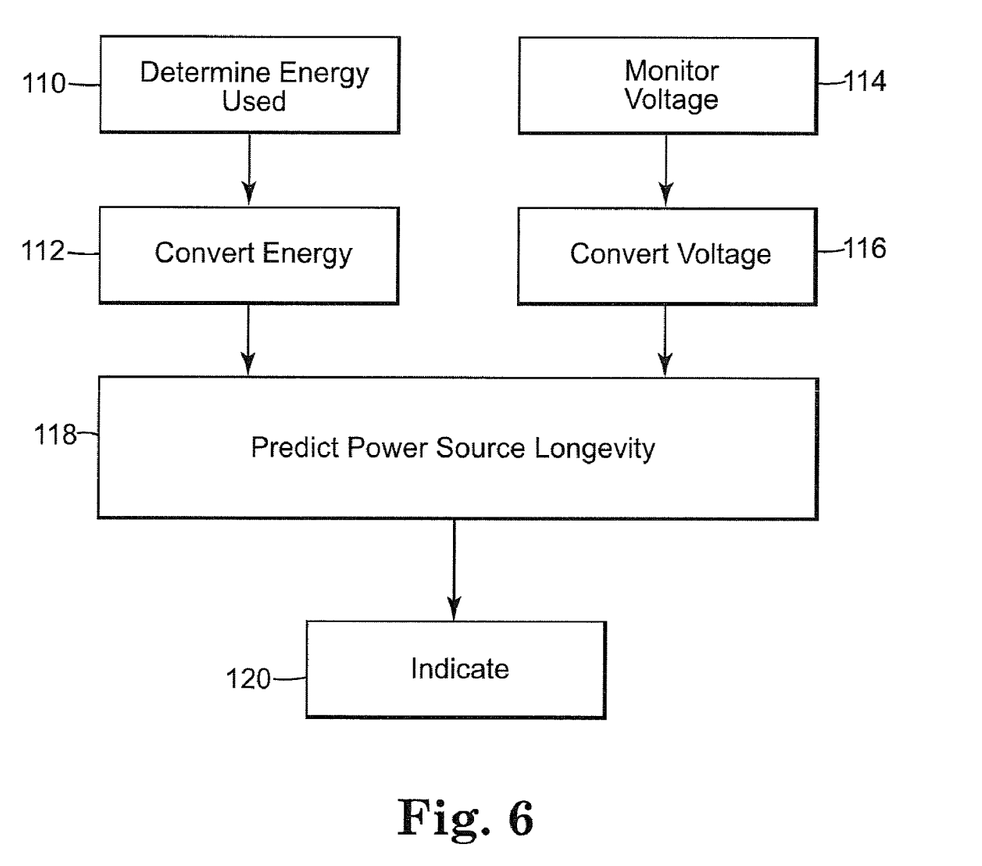
FIG. 6 is a flow chart illustrating the steps of an embodiment of the present invention.

FIG. 6 functionally illustrates a flow chart of the steps of the present invention. The amount of energy consumed by implantable therapeutic delivery device 10 is determined (step 110) and then converted to an estimate of remaining battery useful life (step 112). Possibly simultaneously, the voltage of battery 22 is monitored (step 114) and converted to an estimate of remaining battery useful life (step 116). The longevity of the power source, e.g., battery 22, is then predicted (step 118) using one or the other, or some combination, of the remaining useful life converted from an energy estimate or of the remaining useful life converted from a voltage estimate. Optionally, the longevity of the power source can be indicated (step 120) as, for example, by a visual display or an auditory signal.

It is to be recognized and understood that the power source for implantable therapeutic delivery device 10 may be other than battery 22 described. Other examples of a power source include a capacitive energy source or an inductive energy source.

It is to be recognized and understood that the longevity of the power source may be calculated and communicated in a form other than percentage remaining useful life. Other examples, of longevity calculations include percentage of useful life consumed, amount of time, e.g., minutes, hours, days remaining or used, time to surgery to replacement, and time to schedule for surgical replacement.

Thus, embodiments of the system and method for monitoring power source longevity of an implantable medical device are disclosed. One skilled in the art will appreciate that the present invention can be practiced with embodiments other than those disclosed. The disclosed embodiments are presented for purposes of illustration and not limitation, and the present invention is limited only by the claims that follow.

What is claimed is:

1. An implantable medical device for delivering a therapeutic output to a patient, comprising:
   an electrical power source having a useful life and a voltage which declines over said useful life;

a therapeutic delivery device operatively coupled to said power source and adapted to deliver said therapeutic output to said patient; and a power source longevity monitor operatively coupled to said power source and said therapeutic delivery device, comprising:

an energy counter for counting the amount of energy used by said implantable medical device;

an energy converter for converting said energy used into an estimate of remaining power source longevity and generating an energy longevity estimate;

a voltage monitor for monitoring said voltage of said power source;

a voltage converter for converting said voltage monitored by said voltage monitor into an estimate of remaining longevity of said power source and generating a voltage longevity estimate; and a calculator operatively coupled to said energy converter and to said voltage converter, said calculator predicting said power source longevity using a combination of both of said energy longevity estimate and said voltage longevity estimate.

2. An implantable medical device as in claim 1 wherein said power source longevity monitor further comprises an indicator operatively coupled to said calculator and providing an indication of said power source longevity from said calculator.

3. An implantable medical device as in claim 1 wherein said power source longevity comprises a remaining useful life of said power source.

4. An implantable medical device as in claim 1 wherein said power source longevity comprises an amount of useful life of said power source already consumed.

5. An implantable medical device as in claim 1 wherein said energy converter converts said energy used into an energy longevity estimate by accumulating a count of an amount of energy used by said implantable medical device over at least a portion of said useful life of said power source.

6. An implantable medical device as in claim 1 wherein said energy converter obtains said energy longevity estimate from a look-up table using said amount of energy used.

7. An implantable medical device as in claim 1 wherein said energy converter obtains said energy longevity estimate using a predetermined mathematical algorithm as a function of said amount of energy used.

8. An implantable medical device as in claim 1 wherein said voltage converter obtains said voltage longevity estimate from a look-up table using said voltage.

9. An implantable medical device as in claim 1 wherein said voltage converter obtains said voltage longevity estimate using a predetermined mathematical algorithm as a function of said voltage.

10. A method of monitoring longevity of an electrical power source in an implantable medical device capable of delivering a therapeutic output to a patient, having an electrical power source having a useful life and a voltage which declines over said useful life and a therapeutic delivery device operatively coupled to said power source and adapted to deliver said therapeutic output to said patient, comprising the steps of:

determining an amount of energy used by said implantable medical device;

converting said amount of energy used into an estimate of power source longevity and generating an energy longevity estimate;

monitoring said voltage of said power source;

converting said voltage into an estimate of power source longevity and generating a voltage longevity estimate; and predicting said power source longevity using a combination of both of said energy longevity estimate and said voltage longevity estimate.

11. A method as in claim 10 which further comprises the step of indicating said power source longevity.

12. A method as in claim 10 wherein said power source longevity comprises a remaining useful life of said power source.

13. A method as in claim 10 wherein said power source longevity comprises an amount of useful life of said power source already consumed.

14. A method as in claim 10 wherein said determining step is accomplished by accumulating a count of an amount of energy used by said implantable medical device over at least a portion of said useful life of said power source.

15. A method as in claim 10 wherein said converting said amount of energy step comprises obtaining said energy longevity estimate in a look-up table using said amount of energy used.

16. A method as in claim 10 wherein said converting said amount of energy step comprises obtaining said energy longevity estimate using a predetermined mathematical algorithm as a function of said amount of energy used.

17. A method as in claim 10 wherein said converting said voltage step comprises obtaining said voltage longevity estimate using a predetermined mathematical algorithm as a function of said voltage.

18. A method as in claim 10 wherein said converting said voltage step comprises obtaining said voltage longevity estimate in a look-up table using said voltage.

* * * * *